(12) United States Patent
Bauer et al.

(10) Patent No.: US 8,524,150 B2
(45) Date of Patent: Sep. 3, 2013

(54) DENTAL ALLOY WITH A HIGH GOLD CONTENT THAT IS DEVOID OF PALLADIUM AND COPPER

(75) Inventors: Jochen Bauer, Aschaffenburg (DE); Lothar Volkl, Goldbach (DE); Doris Hathaway, Hanau (DE); Angela Klaus, Hanau (DE); Martin Schuster, Scholkrippen (DE); Rudi Steinke, Hanau (DE)

(73) Assignee: Degudent GmbH, Hanau (DE)

( * ) Notice: Subject to any disclaimer, the term of this patent is extended or adjusted under 35 U.S.C. 154(b) by 922 days.

(21) Appl. No.: 11/665,454

(22) PCT Filed: Oct. 13, 2005

(86) PCT No.: PCT/EP2005/010992
§ 371 (c)(1),
(2), (4) Date: Apr. 16, 2007

(87) PCT Pub. No.: WO2006/040145
PCT Pub. Date: Apr. 20, 2006

(65) Prior Publication Data
US 2008/0152535 A1    Jun. 26, 2008

(30) Foreign Application Priority Data
Oct. 16, 2004   (DE) .......................... 10 2004 050 594

(51) Int. Cl.
*C22C 5/02*   (2006.01)
(52) U.S. Cl.
USPC ......................................... 420/510; 148/430

(58) Field of Classification Search
USPC .................. 148/400, 430; 420/507, 510–512
IPC ............................................ C22C 05/00, 05/02
See application file for complete search history.

(56) References Cited

U.S. PATENT DOCUMENTS

| 4,062,676 A | 12/1977 | Knosp et al. |
| 5,423,680 A | 6/1995 | Prasad |
| 5,453,290 A * | 9/1995 | van der Zel .................. 427/2.27 |

FOREIGN PATENT DOCUMENTS

| DE | 2424575 | 12/1975 |
| DE | 2746525 | 4/1979 |

(Continued)

OTHER PUBLICATIONS

RD 439016, Nov. 2000, Research Disclo, Anonymous.*

(Continued)

*Primary Examiner* — Scott Kastler
*Assistant Examiner* — Vanessa Luk
(74) *Attorney, Agent, or Firm* — Ladas & Parry, LLP

(57) ABSTRACT

A dental alloy with a high gold content that is devoid of palladium and copper. To achieve high mechanical stability, the dental alloy contains between 75 and 95 wt. % Au, between 5 and 20 wt. % Pt, between 0.5 and 3.5 wt. % Zn and/or Sn and/or In, between 0.1 and 0.8 wt. % of an element of a group I, in addition to a single particle refiner of a group II. The weight fraction of the element of group I is between 2 and 6 times that of the single particle refiner of group II, and one element of group I is represented by Nb or Ta or Ti or V and the particle refiner of group II is represented by Ir or Rh.

7 Claims, 5 Drawing Sheets

(56) References Cited

FOREIGN PATENT DOCUMENTS

| | | | |
|---|---|---|---|
| DE | 3132143 | | 3/1993 |
| DE | 10033445 | | 1/2002 |
| DE | 10042316 | | 3/2002 |
| EP | 1193320 | | 4/2002 |
| JP | 09-067628 | * | 3/1997 |
| NL | 9200564 | * | 10/1993 |

OTHER PUBLICATIONS

Professional translation of NL 9200564 (van der Zel), non-English version published on Oct. 18, 1993.*
Professional translation of DE 2755913 (Knosp), non-English version published on Jun. 21, 1979.*
Fischer, "Effect of Small Additions of Ir on Properties of a Binary Au—Ti Alloy", Dental Materials, vol. 18, 2002, pp. 331-335.

* cited by examiner

Typical Inhomogeneous Precipitations

Dendritic Structure
Example 1

Star Structure
Example 2

Inhomogeneous Precipitation
Example 3

Star Structure
Example 4

Comparison Of Structures In Production Batches

Reproducibility Example 5
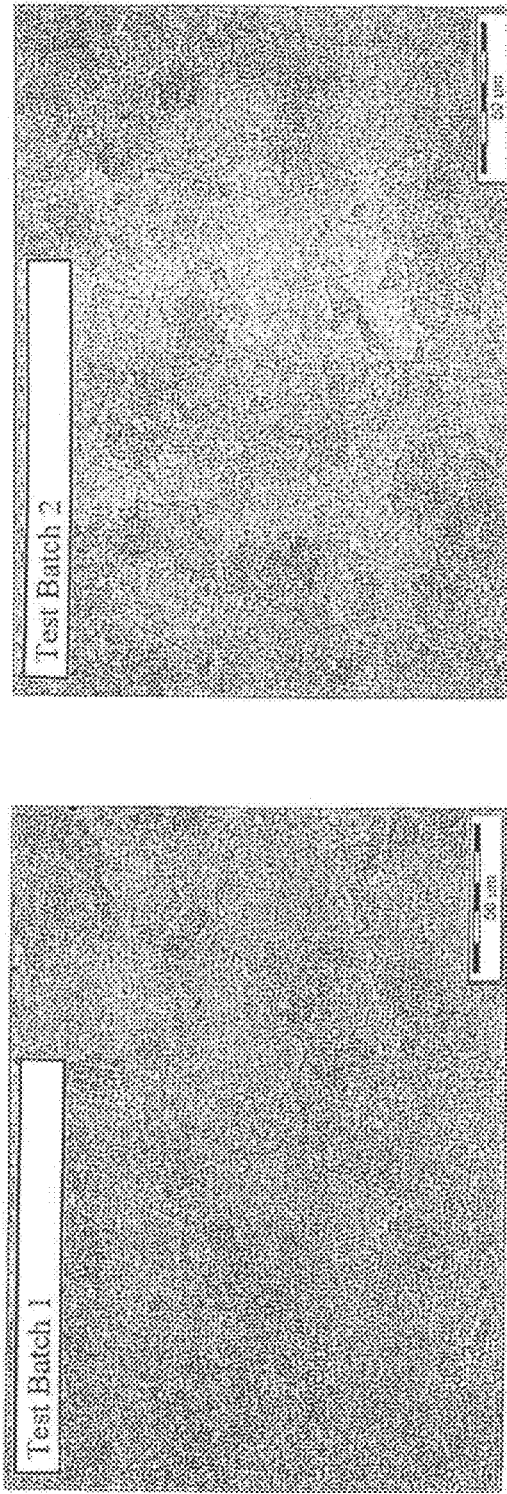
Fig. 9 Test Batch 1
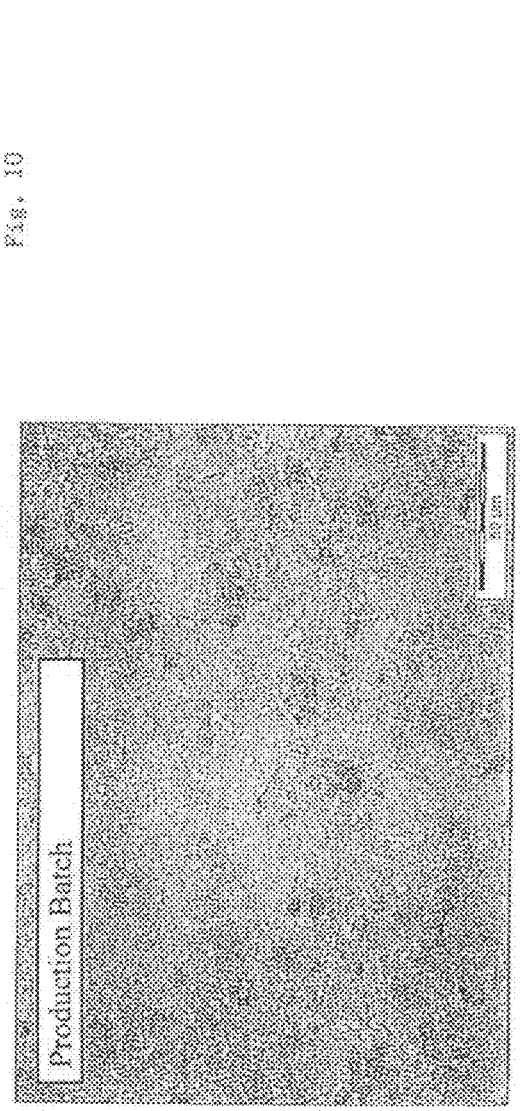
Fig. 10 Test Batch 2
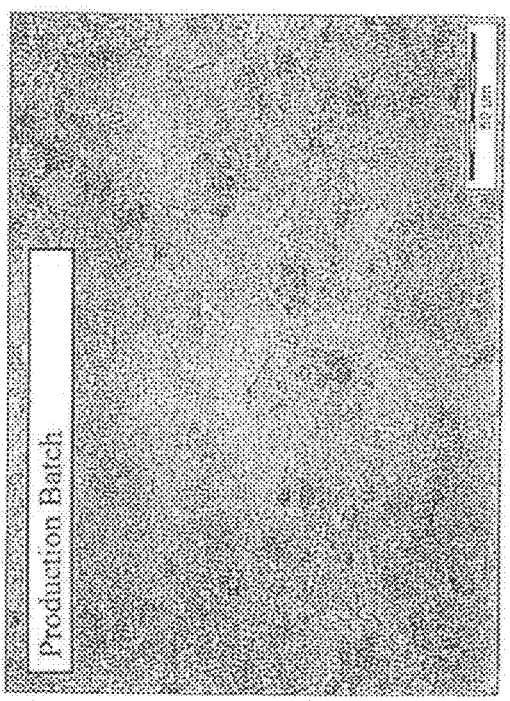
Fig. 11 Production Batch

DENTAL ALLOY WITH A HIGH GOLD CONTENT THAT IS DEVOID OF PALLADIUM AND COPPER

BACKGROUND OF THE INVENTION

The invention relates to a palladium- and copper-free high-gold-content dental alloy, in particular a fire-on dental alloy, for the production of dental prostheses such as dental crowns, bridges, inlays, or onlays, containing at least platinum and at least one particle refiner.

Alloys free of palladium and copper, so-called bio-alloys, are especially used for sensitive patients. The disadvantage of these alloys is the low mechanical stability, especially during ceramic firing, compared to those high-gold-content dental alloys that contain palladium and copper. It must be noted that these particular palladium- and copper-free alloys are prone to distortions. These are caused by so-called creeping of the alloy at high temperatures, the creeping being localized at the particle boundaries.

To achieve increased high temperature stability of Pd—Cu-free high-gold-content dental alloys, one desires precipitation at the particle boundaries. Principal constituents of the precipitation phase contain high-melting elements, with no significant measurable gold content in the precipitation. Platinum is prone to undefined precipitations, which manifest themselves in an inhomogeneous distribution of the phase and in undefined morphology. In extreme cases, this leads to the formation of so-called "stars". Independently of this, distortions arise because of undefined precipitation. Also affected are polishability and millability of the alloy. The optical appearance is affected as the golden color of the alloy fades.

EP-A-1 193 320 discloses a fire-on high-gold-content dental alloy, which contains 80.0 to 86.5% gold, 7.1 to 13% platinum, 0.1 to 8% palladium, 0 to 1.2% silver, 0.7 to 3.5% zinc, 0.0 to 1.0% iron, iridium, ruthenium, rhodium, tantalum, manganese, rhenium, niobium, 0 to 3.5% tin, indium, gallium or 0 to 0.5% copper. A drawback of this particular alloy is its palladium content, which precludes use a bio-alloy.

U.S. Pat. No. 5,423,680 describes a dental alloy, which is free of palladium, gallium, and copper, and possesses a high thermal expansion coefficient. The alloy can contain 50 to 75% Au, 8 to 9% Pt, 12.4 to 38% Ag, 2% In, 1 to 2% Mn, 4% Sn, 1 to 1.9% Zn, 0.05% Ir, and 0.05% $CaB_6$. Platinum, niobium, and tantalum are mentioned as further ingredients.

A noble metal dental alloy in accordance with DE-A-31 32 143 contains 70-80% gold, 1-10% platinum, 5-15% palladium, 0.1-5% tin, 0-5% indium, 0-2% zinc, 0.1-9% silver or copper, 0.0-2% iridium, rhenium, or ruthenium, as well as 0.1-3% cobalt, chromium, gallium, molybdenum, niobium, tantalum, or vanadium.

DE-A-100 33 445 describes a high-gold-content dental alloy that can be copper-free. In accordance with example 1, the alloy is composed of 77.6 wt. % gold, 19.6 wt. % platinum, 2.1 wt. % zinc, 0.6 wt. % tantalum, and 0.1 wt. % iridium.

A high-gold-content alloy in accordance with DE-A-27 46 525 contains a maximum of 0.8 wt. % tantalum and a minimum of 0.5 wt. % rhodium.

DE-A-24 24 575 describes a fire-on gold alloy, which in addition to 80 to 90 wt. % gold, 5 to 15 wt. % platinum, 0.1 to 2 wt. % In, 0 to 2 wt. % tin and 0.05 to 0.5 wt. % Ir also contains 0.5 to 3 wt. % rhodium. Instead of or in addition to rhodium, 0.1 to 2 wt. % tantalum and/or wolfram may be present.

A fire-on gold alloy in accordance with U.S. Pat. No. 4,062,676 contains 60%-90% Au, 5%-35% Pt, 0.1%-3% In, 0%-10% Pd, 0%-3% Sn, 0.5%-3% Rh, 0.1%-2% Ta and/or W, and 0.3%-2% Zn, whereby the weight ratio of the metals of the platinum group relative to zinc, and relative to Ta and/or W is 15-30:1:0.5-1.3.

SUMMARY OF THE INVENTION

The present invention is based on the problem of further developing a palladium- and copper-free high-gold-content dental alloy of the above-mentioned type in a manner that gives rise to high mechanical stability, in particular reproducible high temperature stability.

According to the invention, this problem is solved, essentially, in that the dental alloy, consists of 75 to 95 wt. % Au, 5 to 20 wt. % Pt, 0.5 to 3.5 wt. % Zn and/or Sn and/or In, 0.1 to 0.8 wt. %, of one element of a group I as well as a single particle refiner of a group II, the weight fraction of the element of group I being 2 to 6 times greater than that of the single particle refiner of group II, and Nb or Ta or Ti or V being an element of group I, and Ir or Rh a particle refiner of group II, whereby in the presence of Nb the particle refiner is Ir, in the presence of Ta the particle refiner is Rh, and in the presence of Ti or V the particle refiner is Ir or Rh.

In particular, the dental alloy is composed of 80 to 91 wt. % Au, 7.5 to 18 wt. % Pt, 1 to 2.5 wt. % Zn and/or Sn and/or In, as well as 0.2 to 0.6 wt. % of an element of group I, the weight proportion of the group I element being also 2 to 6 times greater than that of the single particle refiner of group II.

An especially preferred dental alloy according to the invention consists of 80 to 84 wt. % Au, 14 to 17 wt. % Pt, 1.5 to 2.2 wt. % In and/or Sn and/or Zn, 0.3 to 0.5 wt. % of an element of group I as well as a single particle refiner of group II, the weight proportion of the group I element being 2 to 6 times greater than that of the single particle refiner of group II.

The proportions of the elements of the alloy add up to a total sum of 100%.

Preferably, niobium is the group I element and iridium is the single particle refiner, the weight proportion of iridium being, in particular, 0.05 to 0.15 wt. %. In particular, the palladium- and copper-free high-gold-content dental alloy is characterized in that the dental alloy consists of exactly or approximately 81.6 wt. % Au, exactly or approximately 16 wt. % Pt, exactly or approximately 1.4 wt. % Zn, exactly or approximately 0.5 wt. % In, exactly or approximately 0.4 wt. % Nb, and exactly or approximately 0.1 wt. % Ir.

The inhomogeneous distribution of the phase as well as an undefined morphology of the precipitation are the result of a non-directed, non-controlled precipitation kinetic. Elements of the periodic table that are situated directly next to each other, on top of each other, or have a diagonal relation, possess physical and chemical similarity. A related chemical/physical affinity leads, after the nucleation, to a rapid attachment of atoms, and consequently to a preferred growth direction in the structure, which in extreme cases can manifest itself in "star" formation or in dentritic precipitation.

Kinetics of the precipitation formation of this nature can surprisingly be inhibited by employing high-melting elements, which even though they take part in the precipitation phase are chemically or physically dissimilar. Surprisingly, it has been found that in the presence of niobium and the single particle refiner in form of iridium, paying special attention to the ratio of the elements niobium and particle refiner, the high-gold-content dental alloy according to the invention exhibits homogeneously defined precipitation at the particle boundaries, so that the desired mechanical stability and high temperature stability are attainable.

Consequently, in palladium- and copper-free high-gold-content dental alloys, iridium (atomic number 77; configuration 4f14, 5d7, 6s2) and niobium (atomic number 41; configuration 4d4, 5s1) meet the requirements for inhibiting a non-directed and non-controlled precipitation kinetic.

BRIEF DESCRIPTION OF THE DRAWINGS

FIGS. 6, 7, and 9-12 are micrographs of alloys having compositions according to the invention.

DESCRIPTION OF THE PREFERRED EMBODIMENTS

However, a homogeneously defined precipitation at the particle boundaries of palladium- and copper-free high-gold-content dental alloys also takes place if instead of niobium one employs tantalum, vanadium, or titanium with weight proportions corresponding to those of niobium. In the case of tantalum, one employs rhodium as the single particle refiner. If vanadium or titanium is used as replacement for niobium, one can employ iridium or rhodium as the single particle refiner. Independently thereof, the quantitative ratio of tantalum relative to rhodium, or vanadium relative to iridium or rhodium, or titanium relative to iridium or rhodium corresponds to that between niobium and iridium.

Micrographs of alloys according to the invention exhibit very fine precipitation at the particle boundaries over a wide range of gold and platinum contents, the weight proportion of gold being between 80 and 88% and that of platinum being between 10 and 18%.

As a result of the kinetic control of the precipitation, the alloy exhibits, in addition to a high distortion stability, good polishability, millability, and color stability.

Palladium- and copper-free high-gold-content alloys with a composition according to the invention are listed as nos. 5 and 6 in the following table I.

| No. | Au | Pt | Zn | In | Ta | Nb | Ir | Rh |
|---|---|---|---|---|---|---|---|---|
| 1 | 81.3 | 16 | 1.7 | 0.5 | — | 0.2 | — | 0.3 |
| 2 | 85.2 | 11.9 | 1.3 | 0.7 | — | 0.4 | 0.1 | 0.4 |
| 3 | 85.3 | 12.2 | 1.4 | 0.7 | 0.2 | — | 0.2 | — |
| 4 | 81.4 | 16 | 1.7 | 0.5 | — | — | 0.1 | 0.3 |
| 5 | 86 | 11.6 | 1.4 | 0.5 | — | 0.4 | 0.1 | — |
| 6 | 81.6 | 16 | 1.4 | 0.5 | — | 0.4 | 0.1 | — |
| 7 | 84.5 | 12.6 | 1 | 1 | — | 0.3 | 0.1 | 0.5 |
| 8 | 81.5 | 16.0 | 1.4 | 0.5 | 0.4 | — | — | 0.2 |

The high-gold-content alloys listed as nos. 1-4 and 7 are also free of palladium and copper and thus are bio-alloys. However, these either contain more than one particle refiner (alloy no. 2, no. 7) or they contain group I elements and a particle refiner with weight proportions that differ from the teaching of the present invention (alloy no. 1, no. 3). Alloy no. 4 does not contain any elements of group I.

Figure 1:
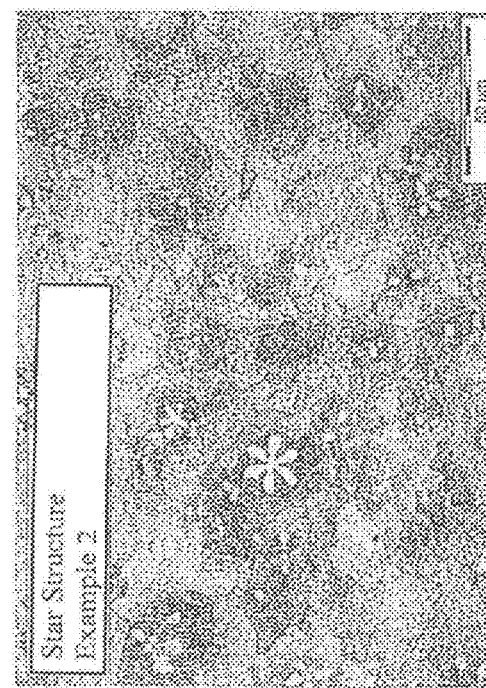
FIGS. 1-5 and 8 are micrographs of alloys which are not according to the invention.
Figure 2:
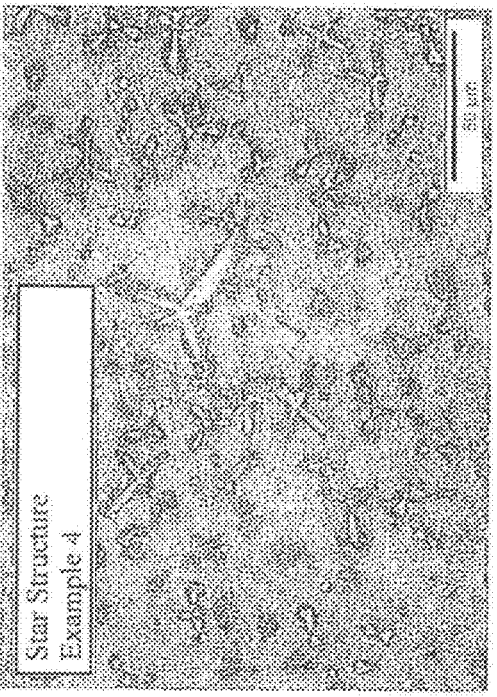
Figure 3:
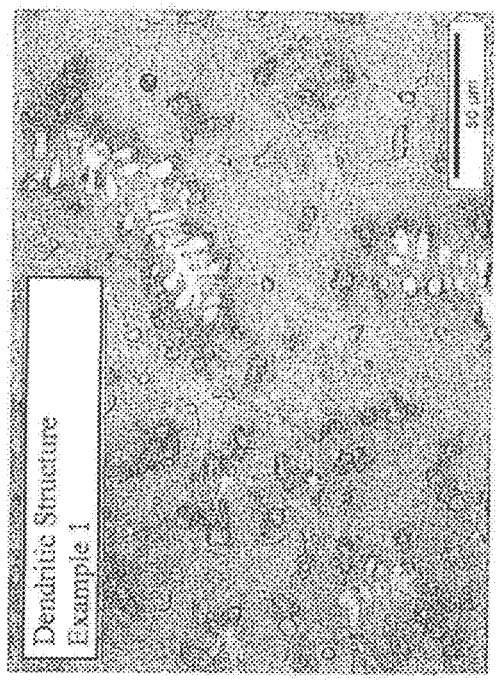
Figure 4:
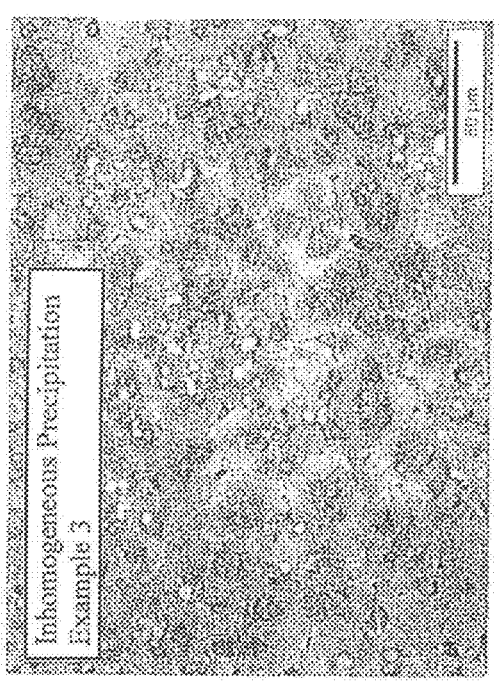
Figure 5:
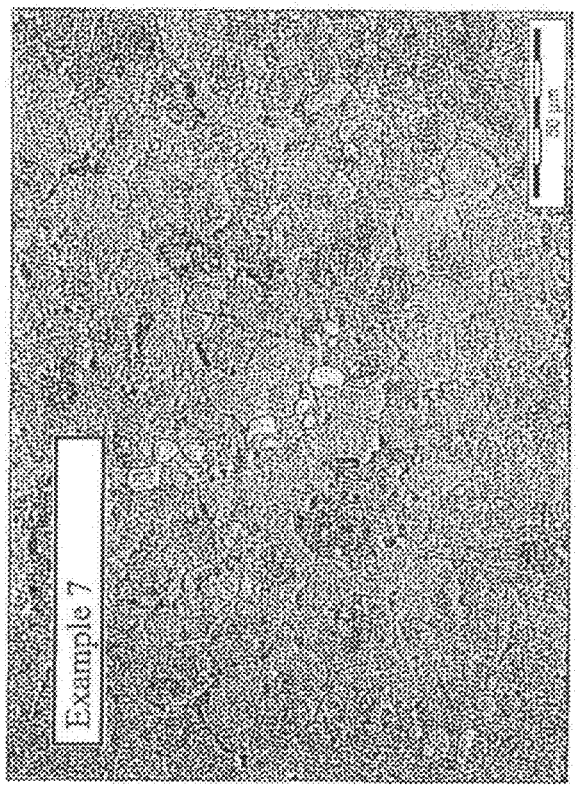

As illustrated by micrographs of alloy no. 1 (FIG. 1), alloy no. 2 (FIG. 2), alloy no. 3 (FIG. 3), alloy no. 4 (FIG. 4), and of alloy no. 7 (FIG. 5), palladium- and copper-free high-gold-content alloys that do not possess the composition according to the invention are prone to undefined precipitation at the particle boundaries, which lead to dentritic structures (FIG. 1), star structures (FIG. 2, FIG. 4), or inhomogeneous distributions (FIG. 3, FIG. 5).

Figure 7:
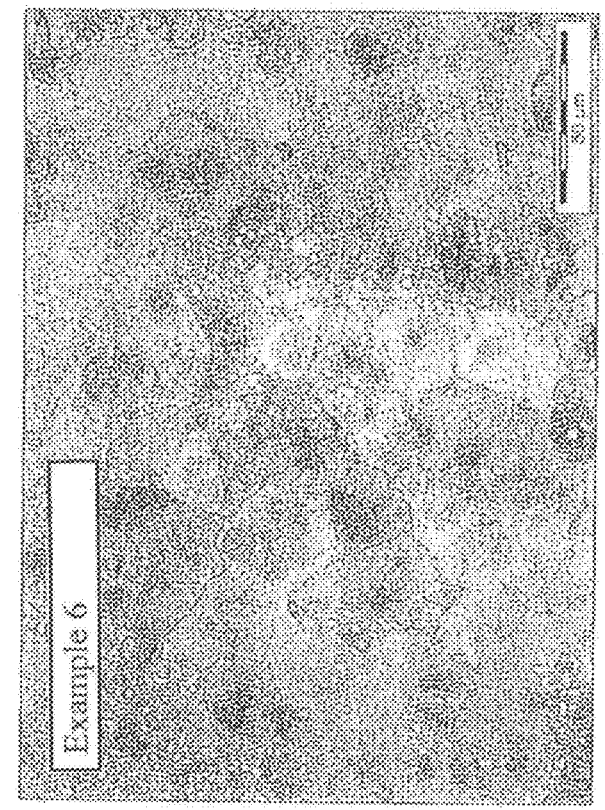
Figure 6:
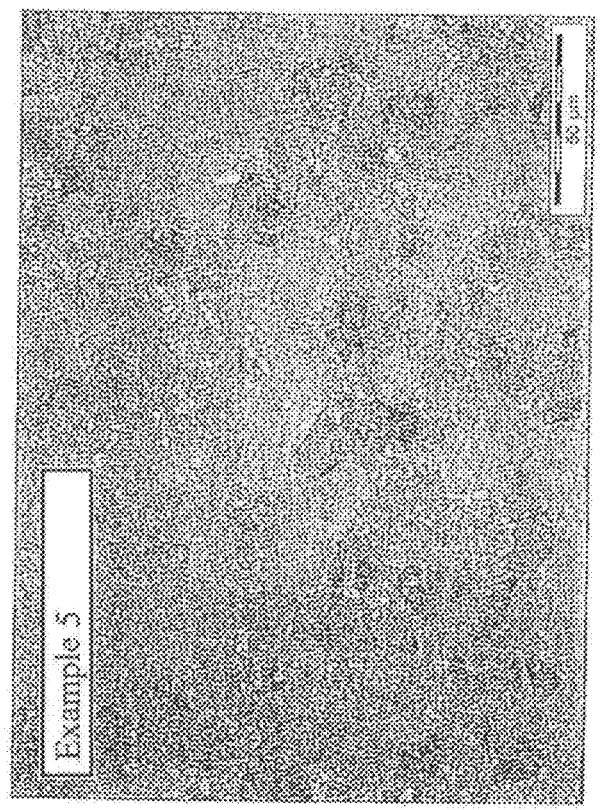
Figure 12:
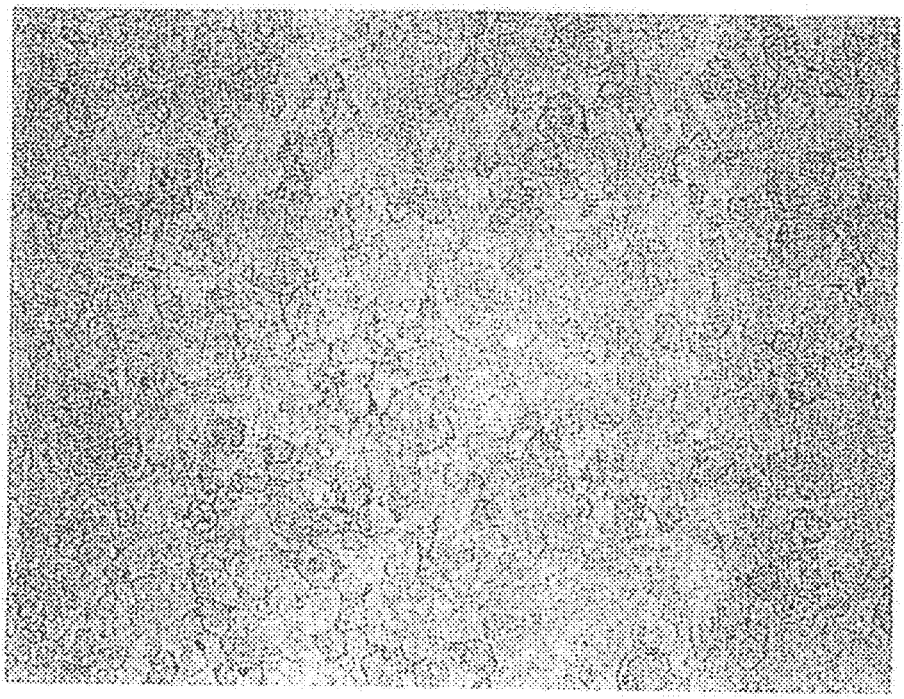

On the other hand, the micrographs of alloy no. 5 (FIG. 6), alloy no. 6 (FIG. 7), and alloy no. 8 (FIG. 12), all of which possess a composition according to the invention, exhibit homogeneous precipitation, which results in high temperature stability, which is particularly important in the firing-on of ceramics, high distortion stability, good polishability and millability. Moreover, these alloys according to the invention exhibit excellent color stability.

Figure 8:
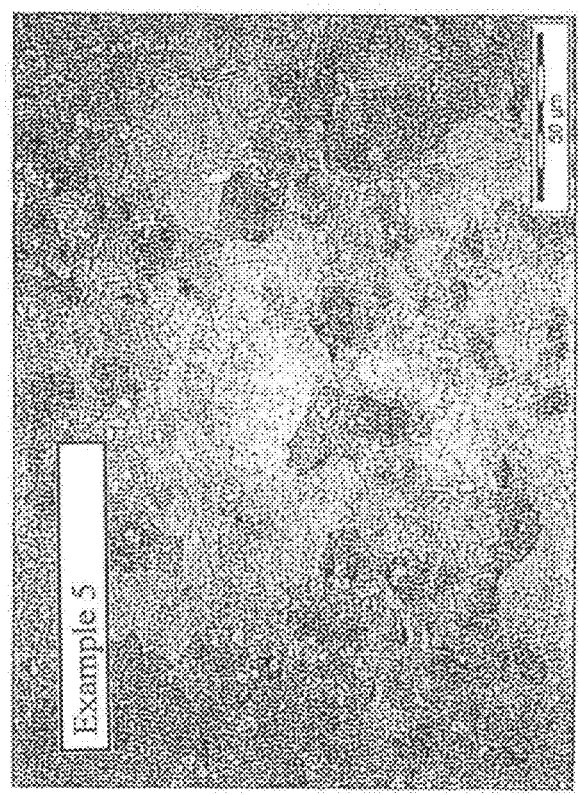

FIG. 8 also shows a micrograph of alloy no. 5, which originates from a production batch. The same is true for alloy no. 7 (micrograph in FIG. 5). The micrograph of alloy no. 5 (FIG. 8) exhibits homogeneous precipitation. In contrast, the micrograph of alloy no. 7 (FIG. 5), which in addition to niobium contains two particle refiners, exhibits inhomogeneous precipitation.

The micrographs in FIGS. 9, 10, and 11 illustrate the reproducibility of the homogeneous precipitation as a result of the niobium:iridium ratio (4:1) specified by the invention in the example of alloy no. 5. Both in alloys with composition no. 5 from test batches (FIG. 9, FIG. 10), as well as in an alloy with composition no. 5 from a production charge, finely distributed precipitations are observed at the particle boundaries, which give rise to the outstanding material characteristics of the cadmium- and copper-free high-gold-content alloy according to the invention.

The invention claimed is:

1. Palladium- and copper-free high-gold-content dental alloy, the dental alloy consisting essentially of, by weight:
   75 to 95% Au,
   5 to 20% Pt,
   0.5 to 3.5% of at least one element selected from the group consisting of Zn, Sn, and In,
   0.1 to 0.8% of an element of a group I element selected from the group consisting of Nb, Ti and V, and
   a single particle refiner of a group II element selected from the group consisting of Ir and Rh,
   wherein the weight proportion of the group I element is 2 to 6 times greater than the group II element,
   wherein when the group I element is Nb, the group II element is Ir, and when the group I element is Ti or V, the group II element is Ir or Rh, and
   wherein said Au, said Pt, said at least one element, said group I element and said group II element make up 100% by weight of said alloy.

2. Dental alloy of claim 1, wherein the group I element is V and the group II element is Ir or Rh.

3. Dental alloy of claim 1, wherein the group I element is Ti and the group II element is Ir or Rh.

4. Palladium- and copper-free high-gold-content dental alloy, the dental alloy consisting essentially of, by weight:
   80 to 91% Au,
   7.5 to 18% Pt,
   1 to 2.5% of at least one element selected from the group consisting of Zn, Sn, and In,
   0.2 to 0.6% of an element of a group I element selected from the group consisting of Nb, Ti and V, and
   a single particle refiner of a group II element selected from the group consisting of Ir and Rh,
   wherein the weight proportion of the group I element is 2 to 6 times greater than the group II element,
   wherein when the group I element is Nb, the group II element is Ir in an amount of from 0.05 to 0.15% by weight of the alloy, and when the group I element is Ti or V, the group II element is Ir in an amount of from 0.05 to 0.15% by weight of the alloy, or R.

5. Dental alloy of claim 4, wherein the group I element is V and the group II element is Ir or Rh.

6. Dental alloy of claim 4, wherein the group I element is Ti and the group II element is Ir or Rh.

7. Palladium- and copper-free high-gold-content dental alloy, the dental alloy consisting essentially of, by weight:
81.6% Au,
16% Pt,
1.4% Zn,
0.5% In,
0.4% Nb, and
0.1% Ir.

* * * * *